US00PP36457P2

(12) United States Plant Patent
Carr

(10) Patent No.: US PP36,457 P2
(45) Date of Patent: Feb. 18, 2025

(54) ***ERYSIMUM* PLANT NAMED 'Cdcery2'**

(50) Latin Name: ***Erysimum* hybrid**
Varietal Denomination: Cdcery2

(71) Applicant: Charles Carr, Winchester (GB)

(72) Inventor: Charles Carr, Winchester (GB)

( * ) Notice: Subject to any disclaimer, the term of this patent is extended or adjusted under 35 U.S.C. 154(b) by 0 days.

(21) Appl. No.: 18/635,091

(22) Filed: Apr. 15, 2024

(30) Foreign Application Priority Data

Dec. 21, 2023 (QZ) ..... PBR 20232807

(51) Int. Cl.
*A01H 5/02* (2018.01)
*A01H 6/20* (2018.01)

(52) U.S. Cl.
USPC ..... Plt./263.1

(58) Field of Classification Search
USPC ..... Plt./263.1, 226
CPC ..... A01H 5/02; A01H 5/00; A01H 6/20
See application file for complete search history.

(56) References Cited

PUBLICATIONS

Beaulieu 2023, BBC Gardeners' World Spring Fair Returns to Beaulieu in April with Spectacular Hillier Secret Garden, retrieved on Aug. 5, 2024 at https://www.beaulieu.co.uk/news/bbc-gardeners-world-spring-fair-returns-to-beaulieu-in-april-with-spectacular-hillier-secret-garden/, 11 pp. (Year: 2023).*

British Association Landscape Industries, Hillier announces new plant introductions for 2023, retrieved on Aug. 5, 2024 at https://www.bali.org.uk/news/hillier-announces-new-plant-introductions-for-2023/#:~:text=The%20Erysimum%20'Colour%20Vibe'%20collections,launched%20by%20Hillier%20this%20year., 2 pp. (Year: 2023).*

Plantipp, Erysimum Colour Vibe Orange, retrieved on Aug. 5, 2024 at https://plantipp.eu/uk/varieties/erysimum-colour-vibe-orange-cdcery2pbr, 2 pp. (Year: 2024).*

* cited by examiner

*Primary Examiner* — June Hwu
(74) *Attorney, Agent, or Firm* — Penny J. Aguirre

(57) ABSTRACT

A new cultivar of *Erysimum* plant named 'Cdcery2' that is characterized by its exhibits foliage that is dark green in color with a densely pubescent surface, its flowers that are warm orange in color with minimal fading, its flowers and leaves that are large in size, its low maintenance, well-branched, and compact plant habit, and its strong and upright stems.

2 Drawing Sheets

Botanical classification: *Erysimum* hybrid.
Variety denomination: 'Cdcery2'.

CROSS-REFERENCE TO RELATED APPLICATIONS

This application claims priority to European Community Plant Variety Office (CPVO) Plant Breeder's Rights Application No. 2023/2807 filed on Dec. 21, 2023, under 35U.S.C. 119(f), the entire contents of which is incorporated by reference herein. This application is also related to a plant breeders' rights application in the United Kingdom on Jan. 4, 2024, Application no. 137/8. The Applicant received the information for the Plant breeders' rights applications directly from the Inventor.

BACKGROUND OF THE INVENTION

The present invention relates to a new and distinct cultivar of *Erysimum* of hybrid origin that is botanically known as *Erysimum* 'Cdcery2'. 'Cdcery2' is a new cultivar of wallflower grown for use as an ornamental landscape plant.

The new cultivar derived from a controlled breeding program by the Inventor in Winchester, United Kingdom. The goals of the breeding program are to create new cultivars of *Erysimum* that perform well in the garden, have large flowers with unique colors that do not fade easily, compact plant habits, and dark green foliage.

The Inventor made crosses between 2011 and 2016 between unnamed and unpatented plants of *Erysimum* in the Inventor's breeding program as both the female and male parents. The seeds were pooled from the crosses and therefore the exact parents are unknown. 'Cdcery2' was selected as a single unique plant in 2018 from the resulting seedlings of the above crosses.

Asexual propagation of the new cultivar was first accomplished by stem cuttings in Winchester, United Kingdom in 2017 by the Inventor in order to evaluate multiple plants. Asexual propagation by stem cuttings and tissue culture using meristematic tissue has determined that the characteristics of the new cultivar are stable and are reproduced true to type in successive generations.

SUMMARY OF THE INVENTION

The following traits have been repeatedly observed and are determined to be the characteristics of the new cultivar. These attributes in combination distinguish 'Cdcery2' as a unique cultivar of *Erysimum*.

1. 'Cdcery2' exhibits foliage that is dark green in color with a densely pubescent surface.
2. 'Cdcery2' exhibits flowers that are warm orange in color with minimal fading.
3. 'Cdcery2' exhibits flowers and leaves that are large in size.
4. 'Cdcery2' exhibits strong and upright stems.

5. 'Cdcery2' exhibits a low maintenance, well-branched, and compact plant habit.
6. 'Cdcery2' exhibits drought resistance and good winter hardiness.

'Cdcery2' can be most closely compared to the *Erysimum* cultivars 'Apricot Twist' (not patented) and 'Winter Spice' (not patented). 'Apricot Twist' is similar to 'Cdcery2' in having flowers that are orange in color. 'Apricot Twist' differs from 'Cdcery2' in having a lower growing habit, narrower leaves, and smaller flowers. 'Winter Spice' is similar to 'Cdcery2' in growth habit. 'Winter Spice' differs from 'Cdcery2' in having a smaller flowers that are lighter orange in color and smaller leaves.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but may not be limited to website listings by Plantago, Hillier, Walter Blom Plants B.V., and Gardens Illustrated.

BRIEF DESCRIPTION OF THE DRAWINGS

The accompanying color photographs illustrate the overall appearance and distinct characteristics of the new *Erysimum*. The photographs were taken of a 6-month-old plant of the new cultivar as grown in a greenhouse in a 21-cm containers in Waddinxveen, The Netherlands.

The photograph in FIG. 1 provides a top view of 'Cdcery2' in bloom.

Figure 1:
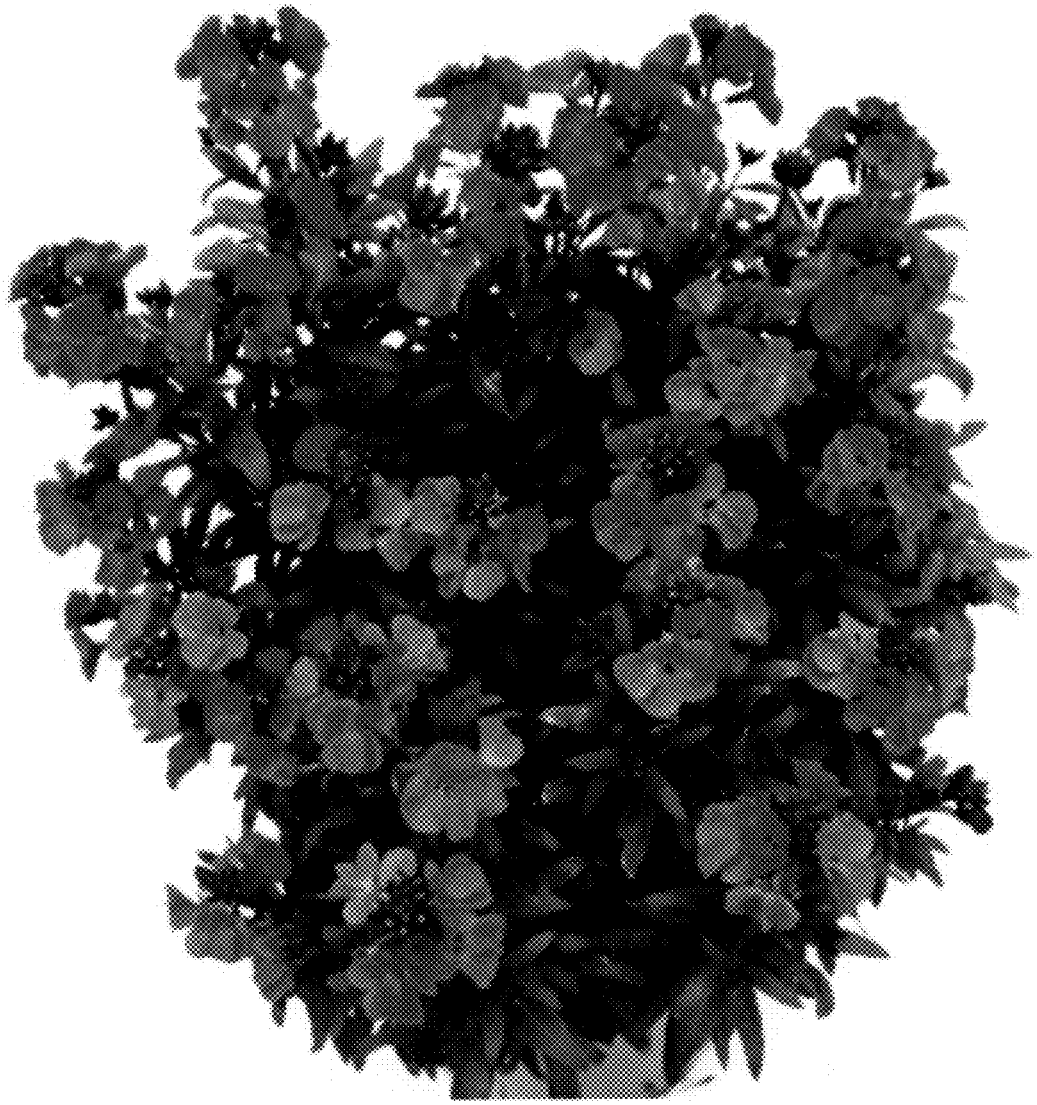
Figure 2:
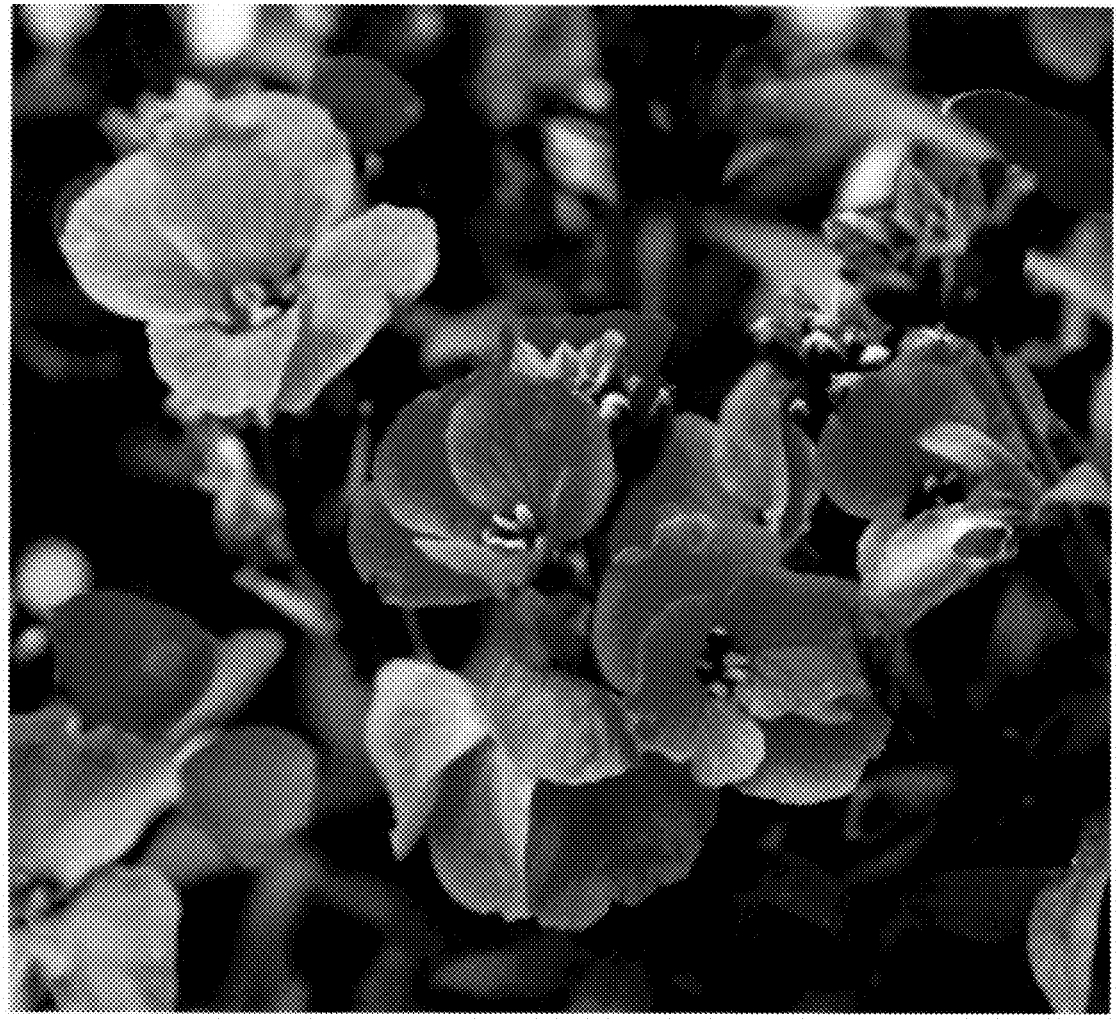

The photograph in FIG. 2 provides a close-up view of the flowers of 'Cdcery2'.

The colors in the photographs are as close as possible with the digital photography and printing techniques utilized and the color codes in the detailed botanical description accurately describe the new *Erysimum*.

DETAILED BOTANICAL DESCRIPTION

The following is a detailed description of 6-month-old plants of the new cultivar as grown in a greenhouse in 21-cm containers in Waddinxveen, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—March to July in The United Kingdom.

*Plant type*.—Herbaceous perennial.

*Plant habit*.—Compact, upright and mounded, and low-growing.

*Height and spread*.—51 cm in height and 39 cm in spread as a 6-month-old plant grown in a container.

*Hardiness*.—At least in U.S.D.A. Zone 6 to 9.

*Diseases and pests*.—No susceptibility or resistance to diseases or pests has been observed.

*Root description*.—Fine, fibrous.

*Propagation*.—Stem cuttings and tissue culture.

*Root development*.—6 to 7 weeks for root initiation, 10 to 12 weeks from a rooted cutting to young plant in a P17 container.

*Growth habit*.—Moderate.

Stem description:

*Stem size*.—Average of 22 cm in length (to base of peduncle) and 8 mm in diameter.

*Stem shape*.—Round.

*Stem color*.—137A to 137C, older wood; 199C with hints of 199A.

*Stem surface*.—Slightly pubescent.

*Stem aspect*.—Held nearly upright.

*Internode length*.—1.5 cm to 2 cm.

*Branching habit*.—Freely branched, an average of 8 lateral stems off one main stem.

Foliage description:

*Leaf shape*.—Narrowly oblanceolate.

*Leaf division*.—Simple.

*Leaf base*.—Attenuate.

*Leaf apex*.—Acute.

*Leaf venation*.—Pinnate, both surfaces 144A in color.

*Leaf margins*.—Entire.

*Leaf attachment*.—Sessile.

*Leaf arrangement*.—Alternate.

*Leaf surface*.—Densely pubescent on both surfaces.

*Leaf color*.—Young and mature upper and lower surface; 137C.

*Leaf size*.—7.5 cm in length and 1.1 cm in width when mature.

*Leaf quantity*.—An average of 24 per stem.

Flower description:

*Inflorescence type*.—Terminal raceme.

*Inflorescence quantity*.—Average of 27 per plant.

*Lastingness of inflorescence*.—Average of 7 days.

*Inflorescence size*.—An average of 6 cm in height and width.

*Flower fragrance*.—Light sweet fragrant.

*Flower number*.—Average of 6 open at one time per inflorescence.

*Flower aspect*.—Upright to outward, dependent on location of the inflorescence.

*Flower bud*.—An average of 1.1 cm in length and 5 mm in width, ovoid in shape, color; N79C, flushed with N77A towards the top.

*Flower type*.—Single.

*Flower size*.—Average of 3 cm in depth and diameter.

*Calyx*.—Tubular in form, an average of 1 cm in length and 8 mm in diameter.

*Sepals*.—4, lanceolate in shape, average of 1 cm in length and 3 mm in width, base truncate, entire margins, surfaces are glabrous, color; inner surface N79C, flushed N79C at the top, outer surface N79A, N77A towards the top.

*Petals.*—4, broadly obovate in shape, obtuse apex, attenuate base, entire margins, an average of 1.5 cm in length and 1.8 cm in width, color; young upper and lower surface 53A, with hints of 59A, 187A towards the edges, mature upper surface a blend of 22A and 53A, older flowers 21B, veins 53A, mature lower surface a blend of 22A, 187A, and 59B, veins 53A, older flowers 59B with hints of 22A, veins 187A.

*Peduncles*.—Round in shape, strong, an average of 12 cm in length and 3 mm in width, pubescent surface, 145A in color.

*Pedicels*.—Round in shape, strong, an average of 5 mm in length, 1 mm in width, pubescent surface, color; 137C, flushed with N77A.

Reproductive organs:

*Gynoecium*.—Pistil; 1, 9 mm in length, stigmas; 1 mm in length, round in shape, 145A in color, style; 6 mm in length, 145C in color, ovary; 144A in color.

*Androecium*.—Stamens; 6, anthers; oblong, 3 mm in length, 4D in color, filaments; adnate to corolla, 7 mm in length, 145B in color, pollen; moderate, 4D in color.

*Seeds*.—Not observed to date.

It is claimed:

1. A new and distinct cultivar of *Erysimum* plant named 'Cdcery2' as herein illustrated and described.

* * * * *